United States Patent
Parienti

[19]

[11] Patent Number: 6,159,013
[45] Date of Patent: Dec. 12, 2000

[54] PORTABLE READING DEVICE FOR THE BLIND

[76] Inventor: Raoul Parienti, 5, Rue de Belgique, 06000 Nice, France

[21] Appl. No.: 09/229,404

[22] Filed: Jan. 11, 1999

[51] Int. Cl.[7] .................................................. G09B 21/00
[52] U.S. Cl. ............................ 434/114; 434/112; 434/113
[58] Field of Search ........................... 434/112, 113, 434/114, 115, 117, 233; 400/109.1

[56] References Cited

U.S. PATENT DOCUMENTS

| | | | |
|---|---|---|---|
| 3,594,787 | 7/1971 | Ickes | 340/407 |
| 3,851,745 | 12/1974 | Okazaki | 434/114 |
| 3,987,438 | 10/1976 | Lindenmueller | 340/407 |
| 3,993,407 | 11/1976 | Moricca et al. | 356/1 |
| 4,033,053 | 7/1977 | Engler | 434/114 |
| 4,194,190 | 3/1980 | Bareau | 340/407 |
| 4,551,102 | 11/1985 | Meinzer | 434/114 |
| 4,571,190 | 2/1986 | Zagler | 434/114 |
| 4,581,491 | 4/1986 | Boothroyd | 434/114 |
| 4,871,992 | 10/1989 | Petersen | 340/407 |
| 4,972,501 | 11/1990 | Horyu | 382/53 |
| 5,091,865 | 2/1992 | Yamada | 395/153 |
| 5,429,507 | 7/1995 | Kaplan | 434/112 |
| 5,466,154 | 11/1995 | Thompson | 434/114 |
| 5,725,379 | 3/1998 | Perry | 434/113 |

FOREIGN PATENT DOCUMENTS

| | | |
|---|---|---|
| 0 542 054 A2 | 5/1993 | European Pat. Off. . |
| 2 493 569 | 5/1982 | France . |
| 2 598 316 | 11/1987 | France . |
| 3 901 023 A1 | 7/1990 | Germany . |

OTHER PUBLICATIONS

Nguyen et al., "A Vocalized Color Recognition System for the Blind," 33 *IEEE Trans. Instrument. Meas.* 122–126 (Jun. 1984).

*Primary Examiner*—Jacob K. Ackun
*Assistant Examiner*—Kurt Fernstrom
*Attorney, Agent, or Firm*—James C. Lydon

[57] ABSTRACT

A portable reading device for the blind consisting of a miniature housing (2) attached to a sleeve to be fitted over the tip of the user's index finger like a thimble. The housing (2) includes an optical sensor array (5) and an electromagnetic unit for displaying one printed character at a time in Braille on a tactile surface as soon as the user's finger passes over the character. The electromagnetic unit contains six electromagnets (7) for reproducing Braille characters, and two further electromagnets for indicating incorrect tracking to the user. The latter two electromagnets are activated when the blind user's finger moves too far up or down as it runs along a line of text.

15 Claims, 3 Drawing Sheets

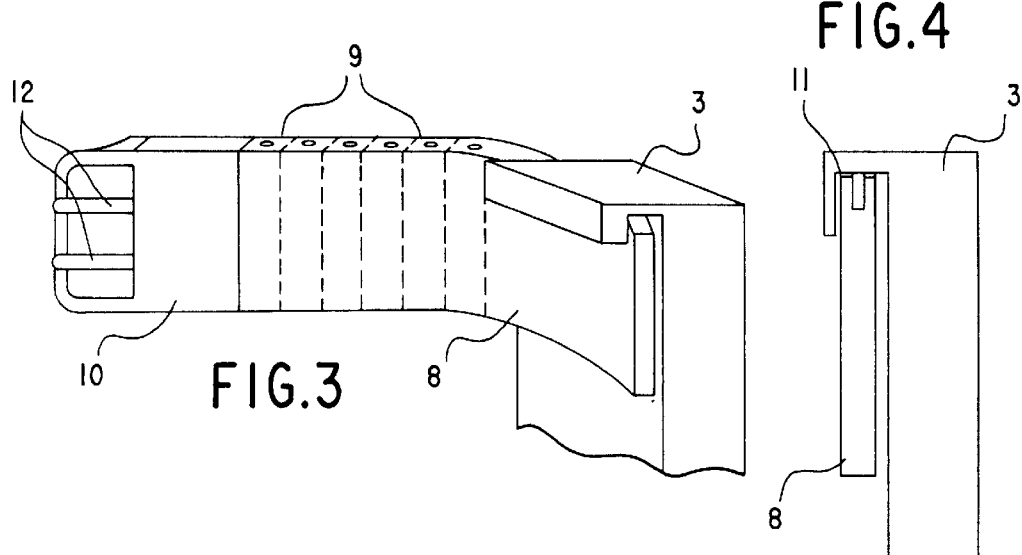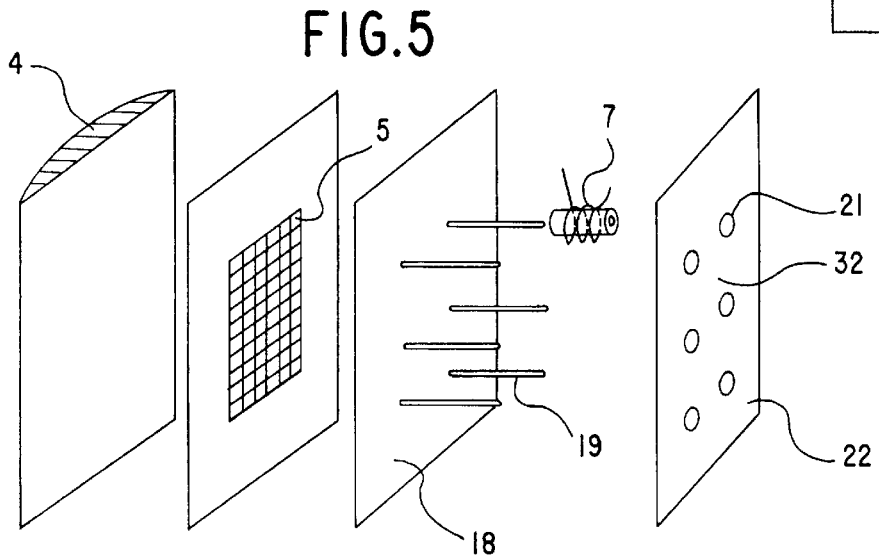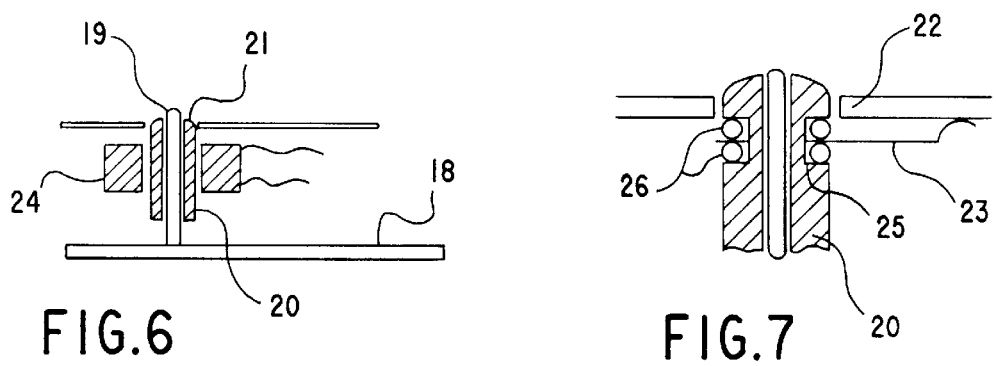

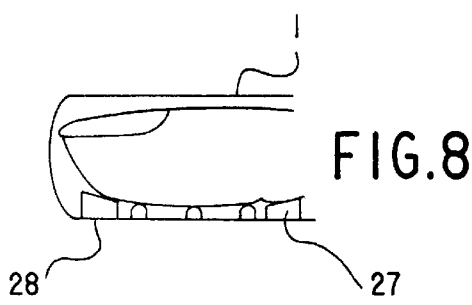
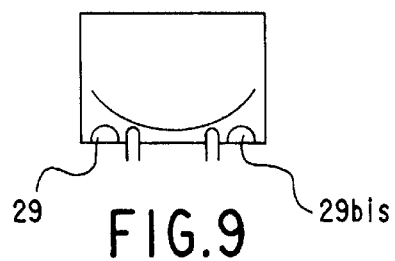
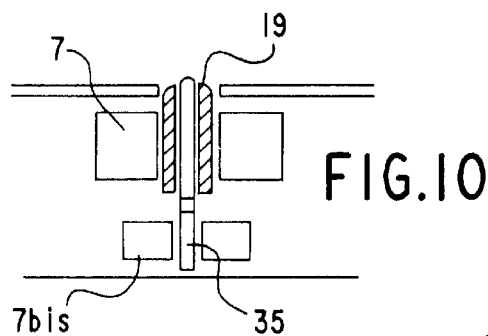
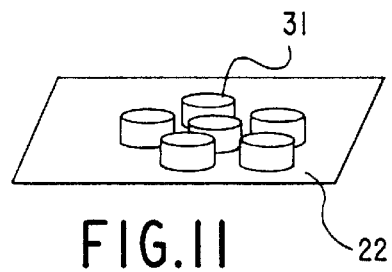
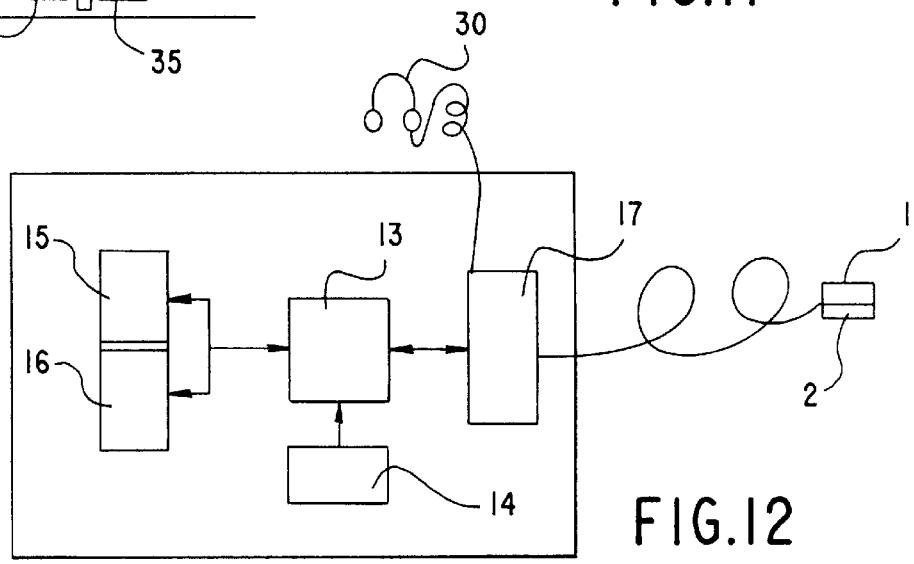
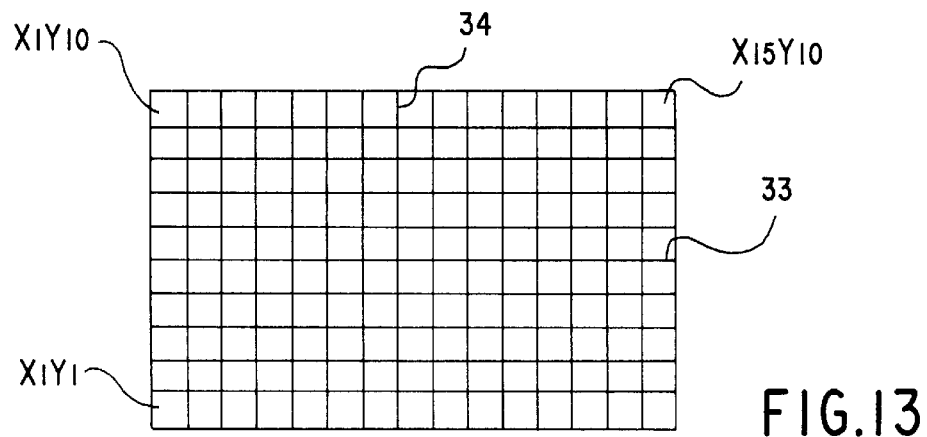

PORTABLE READING DEVICE FOR THE BLIND

BACKGROUND OF THE INVENTION

The present invention describes a portable device for the blind to read traditionally printed texts.

The spectacular development of techniques in computers and electronics has enabled to offer high-performance equipment at attractive prices to a wider and wider range of customers: computers, scanners, printers and fax machines make up everyday tools.

Unfortunately, these breakthroughs had no repercussions for the blind, especially for getting access to reading and, more widely, to culture and knowledge.

The blind can certainly follow radio programmes for accessing cultural or other information. But, to date, they practically have no access to the information they chose. A few experiments appeared here and there to have the blind enjoy books through recorded audio tapes. More recently, other experiments have been carried out for enabling the blind to access reading by using a process that includes text scanning and data processing to have the text appear as Braille sheets. The patent EP-A-0 542 054 sets forth this kind of device.

But, while they are cumbersome and expensive, these processes do not provide any real autonomy.

To date, the salient dots method invented by Louis Braille is widely spread. The blind trained to read in Braille can read very quickly and reach an outstanding level of integration. Unfortunately, only a few books are translated into Braille and their size as well as their price is high.

A few attempts and experiments have been made for portable devices. The patent DE-A-39 01 023 discloses a portable device moved by the blind person over a newspaper properly guided against a side provided for to that end, the text acquired being transcribed into Braille lines.

However, this patent sets forth a device that presents several drawbacks insofar as the blind cannot read Braille exactly as the text is entered. Actually, the device:

requires a guiding device,
is still cumbersome.

The invention disclosed in the present patent can compensate for all these drawbacks.

Actually, by using said invention, the blind person can read any book, newspaper or document printed with traditional fonts with no need for accessories, thanks to a miniature device that has the shape of a sleeve to be fitted over the tip of the user's index finger like a thimble.

SUMMARY OF THE INVENTION

The invention relates to a portable reading device for the blind including optical sensors capable of acquiring printed text, electronics with built-in software for printed character recognition and software for converting said printed characters into Braille characters, and a touch recognition area, characterized in that the reading device comprises a miniature housing attached to a sleeve to be fitted over the tip of the blind person's index finger like a thimble, said miniature housing including an optical sensor array, a touch surface, an electromagnetic unit for displaying one character at a time in Braille as soon as the blind person's finger slides over a printed character, and when said index finger is exactly located over said character. This electromagnetic unit contains six electromagnets for reproducing Braille characters and two further electromagnets for indicating incorrect tracking to the blind person, the latter two electromagnets being activated when the blind person's moves his (her) finger too far up or down as it runs along a line of text.

BRIEF DESCRIPTION OF THE SEVERAL VIEWS OF THE DRAWINGS

The object of the invention will become more apparent from the following detailed description with reference to the accompanying drawings in which:

FIG. 3 shows a variant in which the electronic box is attached to the belt that carries the power source, FIG. 4 shows a detailed view of the connection of the electronic box to the belt, FIG. 5 shows an exploded view of the reading assembly, FIG. 6 is a detailed view showing the action of the electromagnet core operating with the fixed rod, FIG. 7 is an enlargement of the detail quoted in FIG. 6 that highlights the action of small dots (fixed rods) and large dots (mobile cores) in Braille reading, as well as the leaf spring action, FIG. 8 shows the action of mobile positioning indicators located at the upper and lower part of the touch area, FIG. 9 is a cross-section showing lateral bosses, FIG. 10 shows a specific implementation that enables to actuate the small and large dots of Braille writing, the rods thus becoming mobile and comprising at the lower part a ferrous core interdependent with the rods, FIG. 11 shows the action of a plurality of dots forming a "graphic" area, FIG. 12 shows a block diagram of the box electronics, FIG. 13 shows an example for partitioning the field of vision into an array, as well as the related median axis.

DETAILED DESCRIPTION OF THE INVENTION

Figure 1:
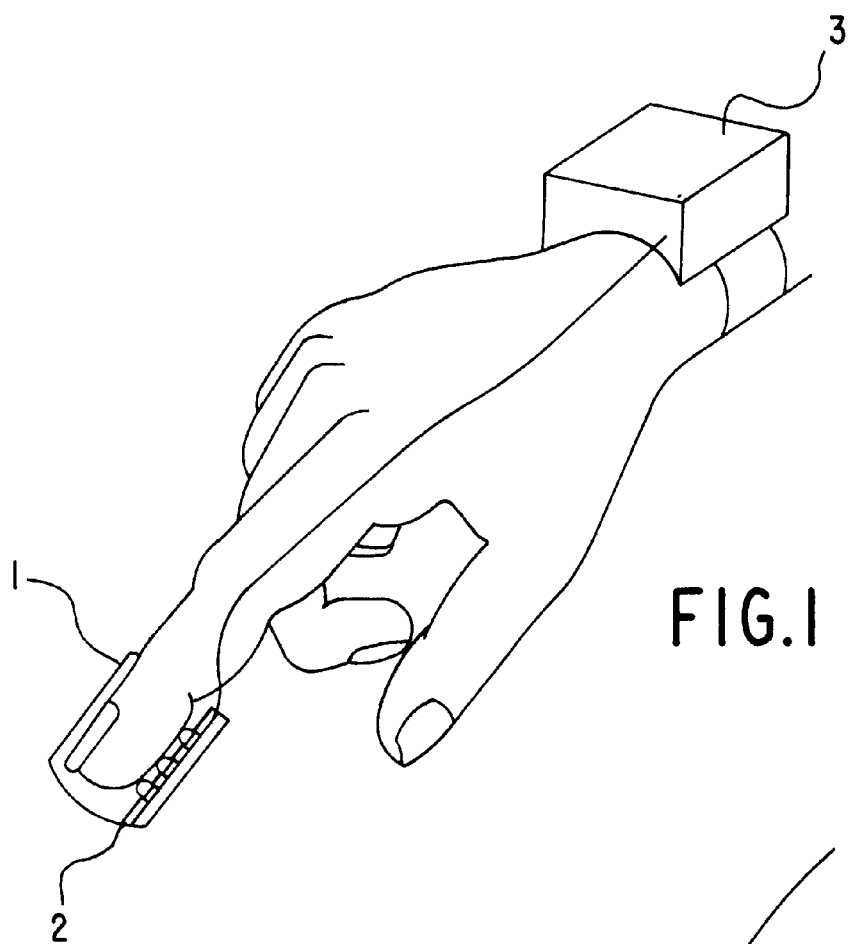
FIG. 1 shows an overall view of the invention, with the sleeve, the housing attached to the sleeve being connected to an electronic box attached to the wrist.

The invention comprises a sleeve (1) to be preferably fitted over the tip of the blind person's index finger, but can also comprise several sleeves fitted over several fingers at the same time. The reading miniature housing (2) is interdependent with the sleeve (1). The set formed by the sleeve (1) and the miniature housing (2) is linked to the electronic box (3) (see FIG. 1).

Figure 2:
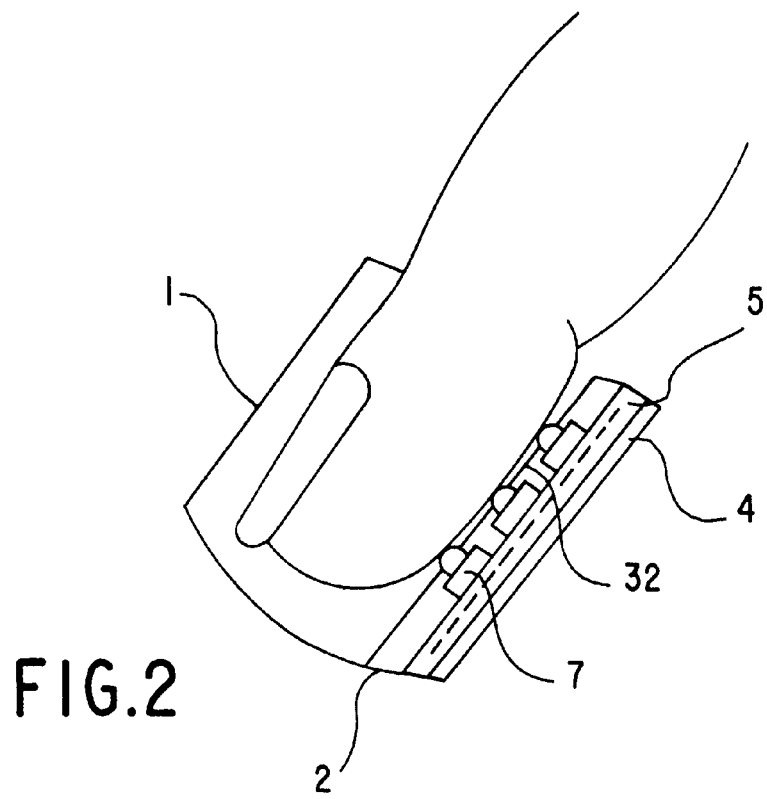
FIG. 2 shows a more detailed view of the reading box with an optical sensor array, a touch recognition unit comprising electromagnets and an optical component.

Let us have a more detailed description of the three sub-assemblies that make up the miniature housing (2), (FIG. 2). This miniature housing is composed of:

a transparent lens (4) for sliding over the text, an optical sensor array (5) made up of a micro-camera based on a pixel array, an electromechanical section (6) that makes up the touch recognition unit and comprises a touch surface (32) in permanent contact with the blind person's index finger pad, the basic version of said touch recognition unit being provided with eight micro-electromagnets (7), six for reproducing Braille characters and two for indicating incorrect tracking to the reader. The latter two tracking electromagnets (27) and (28) will be activated if the blind person's moves his (her) finger too far up or down as it runs along a line of text.

To detect a possible deviation of the blind person's finger when reading, the reference tracking is performed by using the blank line at each line spacing. To that end, the electronics (3) has a built-in positioning software that, on top of performing character recognition and their transcription into Braille, can identify line spacing within a paragraph, or any blank area surrounding a text for stimulating the electromagnets (27) and (28) according to a predetermined code if a deviation occurs. The positioning software can further help the blind person when he (she) has to start a new line at the end of each line. While only the characters read by the central area of the sensors (5) are transcribed into Braille, the characters from the lines located just above and below the line being processed are permanently read in order to accurately identify the end of each line and the beginning of the next line. A specific coding of touch stimulation, for example both electromagnets (27) and (28) simultaneously actuated, indicates the end of line to the blind person. Tracking, that allows the blind person to start exactly at the beginning of a line, is performed similarly through the upper or lower stimulation of electromagnets (27) and (28).

With the present invention, it is as though every character was printed directly in Braille for the blind person.

Let us remind that Braille writing is essentially made up of 80 characters including the whole alphabet with indication of upper cases, punctuation, figures and math operator, as well as other less common operators.

Each character is made up of a mix of large and small dots within an array composed of three rows and two columns. Actually, only the raised large dots represent characters, the small dots, also raised, indicating only the position of large dots within each group of six. To date, modern computer systems use only the large dots in Braille sheets. The invention set forth in the present document uses equally both methods.

The principle of operation is as follows: to read a text, the only thing the blind person has to do is having his (her) index finger, fitted with the miniature housing (2), slide along the text. Said characters are immediately acquired by the microcamera, then recognized by appropriate electronics (3) and the useful signals are sent at once to the micro-electromagnets (7) located in the mechanical section (6).

Each printed character, read by the optical sensors (5) and recognized by the electronics (3) produces the raising of large dots under the blind person's index finger. This way, each printed character from a text will be perceived as a Braille character trough the action of micro-electromagnets driven by an electronic processing unit built into the box (3).

Now, let us describe a particular and more detailed embodiment of the invention: the latter is made up of a sleeve (1) to be fitted over the tip of the user's index finger. A reading unit (2) attached to said sleeve comprises the three sub-assemblies (4), (5) and (6) previously defined.

The whole set of optical sensors (5) is protected by a transparent lens (4) made of glass or non-mineral material, acting as a shield for the sensors (5) and as a focusing device.

When the lens (4) slides over the characters of a text, the latter are acquired by the optical sensors (5) that scan their signals, by using either grey shades (monochrome) or the various colours.

The signals acquired by the optical sensor array (5) are routed to the electronic box (3). This box can be attached to the belt, in the manner of a personal stereo, or to the wrist, like a big watch (see FIG. 1), or in any user's pocket.

However, let us note that as the belt is located close to the user's centre of gravity, this is the best place to carry a load with minimum tiredness.

According to an embodiment of the invention, the belt includes the power supply of the electronic box (3), made up of conventional or even flexible lithium type or the like rechargeable batteries (9), as well as the specific circuit (10), for charging said batteries by simply plugging the belt buckle rods into a mains socket. This convenient feature will make things easier for the blind.

This way, the box (3) that contains the electronics of the invention is preferably attached to the belt (8) and connected to the power supply through a couple of appropriate male and female connectors (11) (see FIGS. 3 and 4). Of course, the belt (8) provided with its power supply and its charging system can feed other devices such as a portable stereo for example.

Now, let us describe the various electronic subassemblies of the box (3). The latter houses a microprocessor (13) driven by a clock (14), said microprocessor handling a RAM (15) and a ROM (16). The ROM contains some Optical Character Recognition software (OCR) and some software for translating any character into its equivalent in Braille. As soon as a character is acquired by the optical sensors (5), the microprocessor (13) gives the necessary instructions for providing the micro-electromagnets (7) with electrical pulses, through a logical circuit (17), to make the character acquired by optical sensors (5) appear in Braille under the user's index finger placed into the sleeve (1).

According to a more sophisticated embodiment of the invention, the optical component (4) can also remotely acquire characters, without any contact with the text to be "translated" into Braille. To this end, the optical component (4) may either be interchangeable or be provided with an "auto-focus" system using well-known processes such as contrast analysis or infrared transmission, to determine the distance between the optical component and the text for performing proper focusing.

Focusing can be performed through a fixed focal length by using the properties of hyper-focal length that gives a sufficient depth of field in order to get a sharp image when the distance between the lens and the text varies from a null distance (lens in contact with the text) to several centimeters.

This remote reading feature will notably enable the processing of large size characters such as book titles.

Now, we are going to describe one of the major components of the invention, namely the mechanical module designed to send touch signals to the blind.

To date, the blind person had to move it's (her) finger along a text transcribed into Braille. Salient dots that characterize the Braille are usually made by embossing some special paper or, with more recent systems, on pin tablets. However, to read the Braille, the blind person had invariably to move his (her) finger over a surface containing the whole raised dots.

The invention disclosed enables to reduce the communication touch surface to its simplest form, namely the surface of the index finger tip.

Thus, the blind person perceives the touch signals through the action of electromagnets.

To perfect the realism of the touch feeling related to the virtual movement of the finger, the electromagnets will not be actuated at the same time to represent each letter, but instead with a small delay:

The salient dots from the first column are activated a few fractions of a second before those from the second column which, in turn disappear a few fractions of a second after those from the first column, to make the next letter appear.

We are going to describe in detail a few non exhaustive embodiments given as examples.

According to the simplest embodiment of the invention, the touch surface of the latter is provided with 6 mobile dots (see FIG. 2).

Another embodiment implements 6 small fixed dots and 6 large mobile dots.

FIG. 5 shows an exploded view of the housing (2) manufactured according to this latter mode and especially the plate (18) on which 6 non metallic rods (19) are made interdependent. The tip of each rod is permanently salient to form the small locating dots. The large dots representing the letters are actually the mobile cores (20) of micro-electromagnets (7), the tip of said cores being rounded. Each core (20) is hollow and crossed by the non-metallic rod (19). This way, when not actuated, only the locating dots are salient and protruding from the six holes (21) located on the upper plate (22) of the touch surface (32) (see FIG. 6). When a micro-electromagnet is energized, the large dot made up by the mobile core (20) will protrude and, thereby, the small dot will disappear (see FIG. 7). A leaf spring (23) will draw the electromagnet core back to its rest position when the electromagnet coil (24) is no longer energized. The leaf spring can usefully act on a groove (25) made in the core (20), by pressing the two flexible O-rings (26) (see FIG. 7).

The inertia resulting from the distortion of the flexible O-rings will provide some progressiveness to the fast movements of the core (20). Along with the slight delay described above between the time of activation of dots from the first and from the second column, this inertia will provide the blind person with a very realistic perception of the virtual movement of the finger over raised characters.

FIG. 10 shows a specific arrangement of the two electromagnets (7) and (7bis), respectively for the large dot and for the small dot. In this embodiment, the touch surface (32) has no raised pattern at rest, as small or large dots appear when a character is translated into Braille.

According to another specific embodiment of the invention, a plurality of mobile rods (31) is implemented. Each small dot is represented by the raising of one rod and each large dot is represented by the raising of several rods (see FIG. 11). This more complex embodiment of the invention will provide the blind person with optimum comfort and touch realism.

Actually, in this embodiment, small and large dots of Braille characters will not appear suddenly under the blind person's finger, but instead they will move progressively like a wave from the right to the left of the index finger, thus giving the exact feeling of a Braille reading performed by sliding the finger over raised characters.

In addition, this embodiment will also enable the "reading" of drawings as the blind person's finger moves over it. The optical sensors (5) will acquire the drawing outlines that will be reproduced raised under the blind person's finger in real time, thanks to the action of electromagnets (7) on the rods.

In a more elaborate version of this embodiment, the optical sensors (5) can handle several contrast levels of the drawing outlines to be acquired, and as a result, the electronics of the box (3) will accordingly send several levels of current intensity to the electromagnets (7) to get several levels of raised pattern formed by the rods (31), depending on the picture to be transcribed.

As explained above, the invention is provided with a tracking device: in order to properly track a text line, the upper and lower parts of the touch surface (32) will be provided with the mobile positioning indicators (27) and (28). If the blind person's finger slightly deviates downward during the reading, the optical system will detect this offset and, upon the order of the microprocessor (13), the lower positioning device (27) will raise under the action of an electromagnet (see FIG. 8). This action will invite the reader to slightly correct his (her) trajectory upward. The upper positioning indicator (28) will operate according to the same principle if the user deviate from the line upward.

To detect any deviation upward or downward, the array will be provided with a set of central optical sensors and with a set of peripheral optical sensors for identifying line spacing and blank areas that surround the text.

The picture of the characters must be received only on the central area of the sensors. The deviation of the character picture to the upper or lower peripheral sensors will produce the stimulation of the upper and lower positioning sensors respectively.

While the touch surface is provided at its upper and lower parts with positioning indicators, the right and left parts are provided with static bosses (29) and (29bis). Each boss is provided with a pressure sensor. A moderate pressure applied on the right sensor (29) will produce the virtual movement of Braille characters under the finger and a higher pressure will speed up the scrolling of said characters if, of course, the latter have been acquired by the sensor and stored into the buffer memory of the RAM (15). On the other hand, a low pressure on the left sensor (29bis) will stop the scrolling and a higher pressure on the same sensor will make the characters scroll in the reverse direction, thus stimulating a finger movement, not from left to right but from right to left, and conversely for languages that read from right to left. The whole set of functions just described come from the processing by the microprocessor (13) of the signals collected by the sensors (29) and (29bis).

According to an additional variant of the invention just described, an audible signal will complete the Braille information provided to the blind person. This way, in parallel to the text decoding by acquiring the characters and translating them into Braille, a discreet earphone (30) connected to the electronics will give out a series of acoustic signals to the blind person's ear. These sound signals will first give the blind person an idea of the page formatting. Actually, the text to be read may be mixed with pictures and arranged in one or several columns. Before the reading, the user will quickly browse the various fields of the page to be "read" with the device fitted over his (her) finger. Blank or coloured passages will be translated by the electronics as a series of specific tones that the user will have to learn first. When the text formatting is memorized, the blind person will be able to acquire the characters efficiently. Moreover, a sound signal will give an idea of the character size. A deeper sound, for example, for large letters and a higher one for small letters, will enable the blind to balance the scrolling speed of his (her) finger over the text.

According to a more sophisticated embodiment of the invention, the optical sensor array is designed for recognizing colours.

The correspondence between visible colours and audible frequencies mentioned above is not only a purely theoretical view, as the term "chromatic" is used for the study of colours as well as for music. In music, the chromatic system is based on the division of an octave into 12 equal parts.

Researches have been carried out to bring out a possible correspondence between colours and sounds.

To give an idea, we will give below an example of correspondence between colours and sound frequencies, as suggested by several books:

If the central C of a piano is tuned to a frequency of 256 periods per second (Hertz), the note G located immediately to the left of the central C will be tuned to 192 Hertz and corresponds to dark red. When going to higher notes, the following correspondence is suggested:

the note G # corresponds to red,
the note A corresponds to orange-red,
the note A # corresponds to orange,
the note B corresponds to yellow,
the note C corresponds to yellow-green,
the note C # corresponds to green,
the note D corresponds to green-blue,
the note D # corresponds to blue,
the note E corresponds to blue-violet,
the note F corresponds to violet, and again the note G of the next octave corresponds to dark red, and so on.

When the blind person moves his (her) finger over the characters, he (she) will perceive their Braille transcription under his (her) finger and, at the same time, he (she) will receive in the earphones (30) a predefined sound signal corresponding to the predominant colour.

When, for example, the blind person is going to read a book title without contact, the sound signal will indicate to him (her) that the predominant colour of the cover is red and that the title is printed in white.

In a more elaborate version of the invention, a scanning of the optical sensor array is carried out by assigning to each associated cell one or more pixels and the matching predefined sound frequency, the sound signal intensity being balanced by the luminous intensity of the scanned cell.

For example, on an elementary 10×16 array with cells numbered from (x1y1) to (x16y10), the electronics starts scanning the cell (x1y1), then the horizontal line (x1y1) to (x16y10) and so on up to the last line (x1y10) to (x16y10) (see FIG. 13).

Any skip to a new line or a new image is characterized by a specific sound signal or by a very short silence, for example a few milliseconds for a new line and a few tens seconds for a new image.

In this "Visual field" scanning process, the whole field will be scanned this way and each time alphanumeric characters are acquired in said field, the system electronics will recognize them and send the corresponding pulses to the electromagnets (7), thus stimulating the user's finger through the translation of acquired characters into Braille.

According to a still more elaborate version of the invention, the latter is provided with an optical component capable of focusing over distances greater than a few centimeters. This way, through the perception of the sounds associated with each field cell, and of the alphanumeric characters included in the field, thanks to the stimulation in Braille of the blind's finger, the latter will get some new autonomy. For example, he (she) will have the opportunity to know that the dominant colour of the shop window in front of him (her) is yellow and that said shop window is topped by a "Baker" shop sign whose dominant colour is red. In a specific version of the invention, the optical sensors (5) can detect infrared "light" and reproduce it though a specific sound frequency to notify the blind of the presence of human beings, animals or heat sources.

In order to reproduce more accurately the image, the centre of the latter will be privileged when scanning. Therefore, the image has two median axis and, when scanning cell after cell, the power of the acoustic signal matching the dominant colour associated with each cell (xnym), already balanced by the cell brightness, increases uniformly from the edges to both median axis, whether it is the vertical (34) or the horizontal one (33), and decreases in the reverse direction.

The increase in the sound signal power can be 1.5 decibel at the vertical median axis and 3 decibels at the horizontal median axis.

The power gain at the centre of the image provides an additional comfort and is similar to what happens with the natural vision. Actually, the natural vision gives priority to what appears in the centre, to the detriment of the sides.

Moreover, the increase power by the centre enables a faster scan of the images containing a small amount of information. For example, if in the image scan discussed above, the cells (x1y1), (x1y2), . . . , (x1y7) receive the same light signal, as the scanned section of the image is invariant, the electronics will not give out seven consecutive sound signals when scanning these seven cells but instead it will give out a single signal whose power variation will help the blind person locate the scanned area.

By using this feature, the blind will understand very quickly that a field is poor in visual information and conversely, he (she) will have the opportunity to stay longer on a field that contains more information. In this version, the optical sensor device associated with the touch surface can usefully be separated from it and be attached on a pair of glasses. In this version, there will be two optical sensor arrays, one of which will be located over the right eye and the other one over the left eye. In this binocular version where the alphanumeric characters appearing on the optical sensor array (5) are still translated into Braille reading at the blind person's finger, the latter receives simultaneously in his (her) right and left ear the sounds resulting from the signals analysed by the sensors placed respectively over the right and the left eye and thus gets a stereophonic perception which, when trained, will help him (her) get a notion of space and, in the long run, have a quasi stereoscopic perception.

Such perception, combined with Braille reading of the whole alphanumeric character set, is likely to provide the blind with a new space of autonomy and freedom.

Finally, by using known techniques already implemented, a derived version of the invention can be produced with speech synthesis software built into the ROM (16), and associated with a dictionary of words and with a corresponding dictionary of phonemes. This way, while he (she) reads in Braille, the blind can listen to the text acquired by the optical sensors (5), possibly translated into the language of its choice through appropriate translation software.

The shapes, sizes and arrangements of the various components, as well as the materials used for the manufacturing, can be changed for equivalent items, without for all that changing the general design of the invention just described.

What is claimed is:

1. A portable reading device for the blind including optical sensors capable of acquiring printed text, electronics with built-in software for printed character recognition and software for converting said printed characters into Braille characters, and a touch recognition surface, characterized in that the reading device comprises a miniature housing (2) attached to a sleeve to be fitted over the tip of the blind person's index finger like a thimble, said miniature housing (2) including an optical sensor array (5) provided with a lens (4), and an electromagnet unit (6) for displaying in Braille one character at a time, on a touch surface (32), as soon as the blind person's finger slides over a printed character and when said index finger is exactly located over said character;

said electromagnetic unit (6) contains six electromagnets (7) for reproducing Braille characters and two further electromagnets (27) and (28) for indicating incorrect tracking to the reader; the latter two electromagnets being activated when the blind person moves his (her) finger too far up or down as it runs along a line of text.

2. A portable reading device for the blind according to claim 1 characterized in that an electronic box (3) has built-in software for identifying line spacing within a paragraph, or any blank area surrounding text, for stimulating the electromagnets (27) or (28) according to a predetermined code if the finger deviates when reading.

3. A portable reading device for the blind according to claim 1 characterized in that the characters from the lines located just above and below the line being processed are permanently acquired by the sensors (5), thus memorizing the beginning and the end of each line, in such a way that coded stimulation from electromagnets (27) and (28) indicates the end of the line and the accurate position of the next line to the blind person.

4. A portable reading device for the blind according to claim 1, characterized in that the activation of large dots representing the letters and made up of mobile cores (20) removes the small fixed dots made up of the rods (19).

5. A portable reading device for the blind according to claim 1, characterized in that each mobile core (20) is hollow and is crossed by the fixed rod (19).

6. A portable reading device for the blind according to claim 1, characterized in that a plurality of mobile rods (31) is implemented: each small dot being represented by the raising of one rod and each large dot being represented by the raising of several rods.

7. A portable reading device for the blind according to claim 1, characterized in that, when the blind person moves his (her) finger over an image, the optical sensors (5) can handle several contrast levels of the drawing outlines, in such a way that the electronics of the box (3) sends in real time the various levels of current intensity to the electromagnets (7) to get several levels of raised pattern formed by the rods (31) to transcribe a picture.

8. A portable reading device for the blind according to claim 1, characterized in that the right and left parts of the touch surface (32) are provided with bosses (29) and (29bis) on which a pressure causes, depending on its direction and intensity, the virtual scrolling of characters to be speed up, stopped or reversed.

9. A portable reading device for the blind according to claim 1, characterized in that the optical component (4) can read characters remotely by using an auto-focus system or the hyper-focal feature of a fixed lens.

10. A portable reading device for the blind according to claim 1, characterized in that a scanning of each field module by the optical sensor array (5) assigns to said module associated with one or several pixels, a predefined sound frequency corresponding to the dominant colour of said module.

11. A portable reading device for the blind according to claim 1, characterized in that skipping from a line to a new line or from an image to a new one during the scanning performed by the sensors (5) produces a specific sound signal or a very short silence, the duration of which is a few milliseconds for skipping to the next line and a few tens milliseconds for skipping to the next image.

12. A portable reading device for the blind according to claim 1, characterized in that the optical sensors (5) can detect infrared "light" and reproduce it though a specific sound frequency to notify the blind of the presence of human beings or animals.

13. A portable reading device for the blind according to claim 1, characterized in that the power of the acoustic signal matching the dominant colour associated with each cell (xnym), increases uniformly from the edges to both median axis (33) and (34) and decreases in the reverse direction.

14. A portable reading device for the blind according to claim 1, characterized in that an optical sensor array is located close to each eye, the sounds resulting from the signals analysed by the optical sensor array (5) placed over the right and the left eye being routed respectively to the right and the left ear, thus providing the blind with stereophonic perception.

15. A portable reading device for the blind according to claim 1, characterized in that a belt includes the rechargeable battery power supply for the electronic box (3) as well as a specific circuit (10) for charging said batteries by simply plugging the belt buckle rods into a mains socket.

* * * * *

UNITED STATES PATENT AND TRADEMARK OFFICE
CERTIFICATE OF CORRECTION

PATENT NO : 6,159,013
DATED : December 12, 2000
INVENTOR(S) : Raoul Parienti

It is certified that error appears in the above-identified patent and that said Letters Patent is hereby corrected as shown below:

On the first page of the patent, please replace

"[22] Filed: January 11, 1999" with the following:

| [22] | PCT Filed: | January 17, 1997 |
|---|---|---|
|  | PCT No.: | PCT/FR97/00096 |
| [86] | § 371 Date: | January 11, 1999 |
|  | § 102(e) Date: | January 11, 1999 |
| [87] | PCT Pub. No.: | WO 97/26639 |
|  | PCT Pub. Date: | July 24, 1997 |

Signed and Sealed this

Eighth Day of May, 2001

*Attest:*

NICHOLAS P. GODICI

*Attesting Officer*  *Acting Director of the United States Patent and Trademark Office*